United States Patent [19]

Cockerill

[11] 4,452,779

[45] Jun. 5, 1984

[54] COMPOSITION AND METHOD OF TREATING LACTATING MAMMALS

[76] Inventor: Vernon L. Cockerill, 1000 Macomb Rd., Rushville, Ill. 62681

[21] Appl. No.: 345,315

[22] Filed: Feb. 3, 1982

[51] Int. Cl.$^3$ .................... A61K 33/42; A61K 33/00
[52] U.S. Cl. .................................. 424/128; 424/127; 424/147; 424/153; 424/154; 424/156; 424/157; 424/162; 424/164
[58] Field of Search ............... 424/127, 153, 154, 162, 424/128, 156, 157, 164

[56] References Cited

PUBLICATIONS

Chemical Abstracts General Subject–10th Col. (1977–1981) page 12849GS.

Primary Examiner—Sam Rosen
Attorney, Agent, or Firm—Marshall, O'Toole, Gerstein, Murray & Bicknell

[57] ABSTRACT

A method and composition for increasing the quantity and quality of the milk produced by lactating mammal subject to lactation failure or MMA syndrome which frequently occurs after giving birth to off-spring and which comprises orally administering to a lactating mammal, such as a farrowing sow or gilt, a composition comprising a combination of diuretic and cathartic components in proportions which maintain the electrolyte balance so as to avoid dehydration of the mammal while effectively removing excess fluid from mammary tissue via the kidneys and the intestinal tract and which in a preferred form is comprised on a weight basis of 65 percent sodium sulfate, 13 percent magnesium sulfate monohydrate, 12 percent sulfur and 10 percent anhydrous potassium sulfate, and said composition preferably being admixed with a complete feed for the lactating mammal in an amount of at least about 0.5 wt. percent or top-dressed on the feed at a rate of one ounce per day for a mammal such as a lactating sow.

19 Claims, No Drawings

COMPOSITION AND METHOD OF TREATING LACTATING MAMMALS

This invention relates generally to a composition and method for increasing the quantity and quality of the milk produced by a lactating mammal and more particularly to a composition and method of removing excess fluids from mammary tissue of a farrowing sow or gilt so as to improve the quantity and quality of the milk produced during farrowing.

A very common complaint among swine producers is that farrowing sows are unable to provide an adequate supply of milk for newly born piglets, because the sow's udders are swollen due to mammary tissue edema. The mammary glands of the farrowing sow may be hard, may have a bacterial infection which contaminates the milk and may have a vaginal or uterine infection. When a lactating mammal exhibits the foregoing symptoms, the mammal is generally said to have "MMA" which is an abbreviation for Mastitis (udder inflamation), Metritis (uterine inflammation) and Agalactia (milk-flow cessation or "lactation failure").

It has been observed that the MMA complex or syndrome is initiated by an accumulation of fluid in the mammary tissue between the milk cells (mammary edema) and frequently occurs in the latter stage of farrowing. The accumulation of fluid compresses the microscopic milk glands so that milk production is reduced or stopped completely. The trapped milk at body temperature is an excellent medium for bacterial growth. Bacteria generally enter through the nipple of the sow and the bacteria reproduce in the milk glands, resulting in tissue infection and fever developing in the mammal. The sows then go "off feed", and the quality and quantity of the milk produced is further lowered.

It is, therefore, an object of the present invention to provide an economical composition and method for preventing the accumulation of excess fluid in mammary tissue of a lactating mammal, particularly farrowing sows or gilts.

It is a further objective of the present invention to provide an economical composition and method for preventing the incidence of MMA syndrome in lactating mammals and particularly in farrowing sows and gilts.

Other objects of the invention will be apparent to those skilled in the art from the following detailed descriptions and claims.

The foregoing objects of the present invention are achieved by providing an orally administrable diuretic and cathartic composition which is preferably in a form suitable for mixing with a complete feed ration for a lactating mammal, such as a farrowing sow or gilt. In the preferred form of the composition the cathartic which is used in combination with the diuretic is preferably comprised of a saline cathartic and an irritant cathartic and contains one or more of each of the following components:

(1) a non-toxic diuretic in an amount effective for withdrawing excess fluid from the mammary tissue into the blood and removing the fluid via the kidneys as urine (i.e. urinary tract);

(2) a non-toxic saline cathartic in an amount effective for withdrawing fluid from mammary tissue into the intestinal tract of the lactating mammal preferably by providing a hypertonic solution in the intestine; and (3) a non-toxic irritant cathartic in an amount effective for readily emptying the contents of the intestinal tract of the lactating mammal, and wherein the several components of the composition preferably provide a source of both potassium and magnesium in addition to sodium and in amounts which maintain a normal electrolyte balance in the body fluids so as to avoid dehydration of the mammal.

A suitable diuretic component for the present composition can be selected from the group comprising potassium sulfate, potassium chloride, potassium tartrate, potassium citrate, potassium acetate, postassium nitrate, sodium sulphate, sodium acid phosphate and tribasic sodium phosphate. Each of the diuretic compounds has at least one ionic component which is absorbed from the intestinal tract into the blood with the compound providing ions which are more readily absorbed being more effective as the diuretic.

A suitable saline cathartic or laxative component can be selected from the group comprising potassium sulfate, potassium chloride, sodium sulfate, sodium chloride, sodium phosphate, sodium tartrate, sodium citrate, magnesium sulfate, magnesium phosphate, magnesium oxide, magnesium hydroxide, magnesium tartrate, and magnesium carbonate. The compounds which are less readily absorbed are preferred for use as the saline cathartic component of the composition and for providing a hypertonic solution in the intestinal tract. The saline cathartics preferably form a hypertonic solution in the intestine and the water draining into the intestine by osmotic pressure significantly increases the liquid bulk within the intestine which has an effect similar to other bulk cathartics or laxatives. Where a large amount of a bulking agent is used in combination with the composition the amount of the cathartic used in the composition can be reduced.

Since both magnesium and potassium ions, but not sodium ions, are removed by excretion in the urine even when there is a deficiency of potassium and magnesium ions in the body of the mammal, a source of both magnesium and potassium ions are preferably included in the composition in order to maintain the required electrolyte balance of magnesium, potassium and sodium. It will be evident that the saline cathartic is used in the composition to perform the multiple functions of drawing water into the intestines which stimulates defecation from the intestinal tract and provides a source of potassium and/or magnesium for maintaining the electrolyte balance.

An irritant cathartic, such as sulfur or barium chloride, is generally included as a component of the present composition in order to improve removal of the liquified feces from the intestinal tract, since a confined sow or other mammal during farrowing and lactation are recumbent much of the time. In some instances, however, the irritant cathartic may not be essential, as when a larger amount of a saline cathartic, such as sodium sulfate, is used in the composition. It will be apparent that the amounts of the saline cathartic and irritant cathartic used in the composition have an inverse relationship, since in some instances the saline cathartic can perform the same function as the irritant cathartic.

Depending on the availability and cost of the several diuretic and cathartic ingredients which can be used in the composition of the present invention for withdrawing excess fluid from the mammary tissue and effecting removal of the said fluids from the lactating mammal, other non-toxic salts and materials can be used in place of the above specified exemplary ingredients.

A preferred combination of ingredients which is very effective for removing excess mammary fluids from farrowing sows when mixed with a complete farrowing and lactation feed to form one ton (2000 lbs.) of a feed for farrowing sows has the following formulation of ingredients:

|  |  | Wt. % |
|---|---|---|
| Sodium sulfate anhydrous | 6.5 pounds | 65 |
| Magnesium sulfate monohydrate | 1.3 pounds | 13 |
| Potassium sulfate anhydrous | 1.0 pound | 10 |
| Sulfur | 1.2 pounds | 12 |
| Total Wt. | 10.0 pounds | |

In the foregoing composition which is intended for admixing with a complete farrowing feed composition for sows to form 2000 pounds of feed composition the sodium sulfate is made the major constituent, because the sodium sulfate is relatively non-toxic, is an effective saline cathartic and has significant diuretic properties. The potassium sulfate is used in combination with the sodium sulfate because small amounts of potassium sulfate are effective as a saline laxative and in addition has diuretic properties. The potassium sulfate also provides a replacement source of potassium which prevents a blood potassium deficiency. The magnesium sulfate, while having saline laxative properties, is used primarily as a source of magnesium to prevent hypomagnesia which otherwise would result due to the diuretic effect of the sodium sulfate and potassium sulfate components of the composition. The saline cathartic effect of the magnesium sulfate when used in the amount specified in the foregoing formulation after mixing with the feed is very insignificant. In order for magnesium sulfate to function as a saline cathartic the magnesium sulfate heptahydrate would have to be increased from the 1.3 pounds used in the foregoing formulation to between about 5.5 and 16.5 pounds.

The foregoing composition containing the preferred ingredients or their equivalents, can also be top-dressed on a sow feed or other mammal feed rather than being mixed with the feed material. When top-dressed on a feed for lactating sows the composition is used at a rate of about one (1) ounce per day for each sow.

The concentration of the preferred ingredients can be varied considerably within the safe and effective limits of each ingredient in order that the resulting composition contain safe and effective amounts for providing the required diuretic and cathartic effects for safely and effectively withdrawing excess fluid from the mammary tissue of a lactating mammal without dehydrating the mammal. Thus, the anhydrous sodium sulfate can be used per ton of a complete feed for sows within the range of about 1 to 8 pounds, the anhydrous potassium sulfate within a range of about 1 to 5 pounds, the magnesium sulfate monohydrate within a range of about 1 to 9 pounds and sulfur in the form of elemental sulfur flour within a range of about 1 to 5 pounds.

The foregoing composition can be provided as a concentrate or premix in a finely divided form suitable for uniformly dispersing in a dry carrier which can be ingested by the mammal and can have various nutritional and/or medicinal ingredients included therein. For example, the composition can include additives which improve the nutrition value thereof and the health of the mammal, including vitamins, mineral supplements and specific compounds, such as iron salts or complexes which increase the iron content in both the blood and the milk of the mammal. Among the suitable iron salts or compositions is the ferrous glycine complex (U.S. Pat. No. 4,183,947) which can be included in the foregoing formulation in an amount of about one pound.

The composition of the present invention in the form disclosed is preferably uniformly dispersed in or applied as a top dressing to a complete feed for the mammal, since it is important to maintain the highest possible nutritional level in the lactating mammal during farrowing. The composition is preferably mixed with a high energy ration which contains a substantial amount of quality protein so that the quality and quantity of the milk produced is high. It is also important that the composition is mixed with a complete feed which is palatable to the lactating mammal, such as a sow or gilt, in order to assure consumption of an adequate amount of the composition daily.

In order to increase the palatability of the complete feed and provide an adequate amount of roughage, the bulking component of the complete feed should be carefully selected and preferably provided mainly from oats or high quality alfalfa meal while avoiding using wheat bran and poor quality alfalfa or ground hay which do not have a taste acceptable to sows, particularly in warm weather.

A suitable high energy complete ration for farrowing sows and gilts containing the diuretic and cathartic composition of the present invention which can be prepared at the point of consumption from ingredients readily available to a swine producer has the following composition:

| Soybean Meal | 350 lbs. |
|---|---|
| Oats | 300 lbs. |
| Corn | 1262 lbs. |
| Calcium Carbonate | 17 lbs. |
| Dicalcium Phosphate | 40 lbs. |
| Salt | 5 lbs. |
| Ferro Glycine Complex | 1 lb. |
| Vitamin-Mineral Premix | 15 lbs. |
| D&C Composition[1] | 10 lbs. |
| | 2000 lbs. |

[1]The diuretic and cathartic composition of the present invention.

A farrowing-lactation ration of the foregoing composition with which the present composition is mixed contains the following amounts of protein, calcium, phosphorous and fiber:

| Protein | 15.00% |
|---|---|
| Calcium | .86% |
| Phosphorous | .73% |
| Fiber | 3.80% |

If desired, the complete ration for sows can be made using standard prepared feed supplements which are available in the market, such as a 36% Supplement, 40% Mixed Supplement, and Base Mix with the balance mainly corn and oats or alfalfa meal. Each complete ration should preferably contain as bulking ingredient about 300 pounds of oats or 150 pounds of alfalfa meal. The feed formulation preferably should contain all of the required vitamins and minerals for a farrowing sow.

The diuretic and cathartic composition of the present invention when mixed with a complete feed ration for lactating sows so as to constitute at least about 0.5 wt. percent thereof is preferably fed to a farrowing sow or gilt beginning 10 to 14 days before farrowing and is continued until weaning. The sows should consume at least about 12 pounds and a gilt about 10 pounds of the combined feed mixture daily, and to insure adequate consumption, the ration must be made available to the sows and gilt continuously (i.e. full fed) and an unrestricted supply of water should be made available to the sows. Since the saline cathartics and diuretics are more effective when consumed by single or "simple" stomached mammals and less effective in ruminants, the concentration of the ingredients in the composition when intended for ruminants instead of sows should be increased to provide safe and effective amounts which promote effective removal of excess fluid.

The diuretic and cathartic composition of the present invention when mixed with a complete high energy ration for sows and consumed in the recommended quantity as described herein is adapted to keep fluid from accumulating or remaining in the udders of mammals by drawing fluid from mammary tissue very gradually, clean the intestinal tract of the sow and reduce toxin accumulation (from retained feces) that throws sows off feed, supply high energy to the sow that increases milk fat and milk flow without causing fluid accumulation in the mammary tissue, prevent overeating and diarrhea or constipation caused by low fiber diets by including sufficient bulk in the complete feed mixture, reduce the hypoglycemia (low blood sugar) incidence in the piglets and increase the resistance of the piglets to stress by increasing the quantity and quality of the sow's milk.

The composition of the present invention by having the disclosed combination of diuretic and cathartic ingredients in proportions which effectively withdraw excess fluid from mammary tissue of a lactating mammal and effect excretion thereof without causing dehydration of the mammal significantly increases the survival rate of the offspring of mammals by increasing the quantity and quality of the milk available to the offspring; and thereby prevent the offspring suffering from malnutrition which is a major cause of death of newly born mammals.

I claim:

1. A method of removing an accumulation of fluid from the mammary tissue of a lactating mammal comprising orally administering to said lactating mammal a composition comprising in combination at least one non-toxic diuretic salt in an amount effective for drawing fluid from mammary tissue into the urinary tract of the mammal and at least one non-toxic saline cathartic salt in an amount effective for drawing fluid from the mammary tissue into the intestinal tract of the mammal and emptying the contents of the intestinal tract of the mammal, and said diuretic and cathartic salts providing a source of sodium, potassium and magnesium in a proportion required to maintain a normal electrolyte balance in the fluids of said mammal so that dehydration of the mammal is avoided.

2. A method as in claim 1, wherein said composition contains about 10 percent by wt. of a ferrous glycine complex.

3. A method of removing an accumulation of fluid in mammary tissue of a lactating mammal comprising; orally administering a non-toxic composition in an amount effective for drawing fluid from mammary tissue of a lactating mammal into the intestinal and urinary tracts and for emptying the contents of said intestinal tract while maintaining a normal electrolyte balance in the body fluids of said mammal which contains on a wt. basis about 65 percent anhydrous sodium sulfate, about 13 percent magnesium sulfate monohydrate, about 12 percent sulfur, and about 10 percent anhydrous potassium sulfate.

4. A method as in claim 3, wherein 10 pounds of said composition are mixed with a complete feed for a lactating single stomached mammal to form about 2000 pounds of the mixed feed, and allowing said mammal to full feed on said mixed feed.

5. A method as in claim 3, wherein said composition is fed orally to a sow at least 10 days prior to said sow giving birth to offspring and continuing feeding said composition to said sow until weaning of said offspring.

6. A method as in claim 3, wherein said feed is a complete high energy feed containing at least about 150 pounds of a bulky feed material.

7. A method as in claim 3, wherein said composition is top-dressed on a complete feed for a lactating single stomached mammal at a rate of one ounce per day.

8. An orally administrable composition for removing fluid from mammary tissue of a lactating mammal comprising in combination; at least one non-toxic diuretic salt in an amount effective for drawing fluid from said mammary tissue into the urinary tract and at least one non-toxic saline cathartic salt in an amount effective for drawing fluid from said mammary tissue into the intestinal tract of said mammal and for causing the contents of the intestinal tract of said mammal to be excreted, and said diuretic and cathartic salts providing a source of sodium, potassium, and magnesium in an amount effective for maintaining normal electrolyte balance in said mammal; whereby excess fluid is withdrawn from said mammary tissue while avoiding dehydration of said mammal.

9. A composition as in claim 8, wherein said composition contains about 10% of a ferrous glycine complex.

10. An orally administrable composition for removing an accumulation of fluid in mammary tissue of a lactating mammal comprising; a non-toxic composition effective for drawing fluid from mammary tissue of a lactating mammal into the intestinal and urinary tracts and for emptying the contents of said intestinal tract while maintaining a normal electrolyte balance in the body fluids of said mammal which contains on a wt. basis about 65% anhydrous soldium sulfate, about 13% magnesium sulfate monohydrate, about 12% sulfur, and about 10% anhydrous potassium sulfate.

11. A feed composition for a lactating mammal comprising; a complete feed ration for a lactating mammal containing at least about 0.5 percent by wt. of a composition having in combination as the essential ingredients thereof at least one diuretic salt in an amount effective for drawing fluid from the mammary tissue into the urinary tract of said mammal and at least one saline cathartic salt in an amount effective for drawing fluid from a mammary tissue of said mammal into the intestinal tract of said mammal and for causing the contents of the intestinal tract of said mammal to be excreted, and said diuretic and cathartic salts providing a source of sodium, potassium, and magnesium in an amount which maintains a normal electrolyte balance in said mammal; whereby excess fluid is withdrawn from said mammary tissue while avoiding dehydration of said mammal.

12. A feed composition for removing an accumulation of fluid in mammary tissue of a lactating mammal comprising; a complete feed ration for a lactating mammal containing at least about 0.5 wt. percent of a composition effective for drawing said fluid from mammary tissue of a lactating mammal into the intestinal and urinary tracts and emptying the contents of the intestinal tract while maintaining a normal electrolyte balance in the body fluids of said mammal which contains on a wt. basis about 65% anhydrous sodium sulfate, about 13% magnesium sulfate monohydrate, about 12% sulfur, and about 10% anhydrous potassium sulfate.

13. A feed composition as in claim 11, wherein said composition contains about 10% of a ferrous glycine complex.

14. An orally administerable composition for removing an accumulation of fluid from mammary tissue of a lactating mammal comprising:
  (1) at least one non-toxic diuretic salt in an amount effective for drawing excess fluid from mammary tissue of a lactating mammal into the urinary tract of said lactating mammal selecting from a group consisting of potassium sulfate, potassium chloride, potassium tartrate, potassium citrate, potassium acetate, potassium nitrate, sodium sulphate, sodium acid phosphate and tribasic sodium phosphate;
  (2) at least one non-toxic saline cathartic salt in an amount effective for withdrawing excess fluid from mammary tissue into the intestinal tract of said lactating mammal which is selected from the group consisting of potassium sulfate, potassium chloride, sodium sulfate, sodium chloride, sodium phosphate, sodium tartrate, sodium citrate, magnesium sulfate, magnesium phosphate, magnesium oxide, magnesium hydroxide, magnesium tartrate, and magnesium carbonate; and
said diuretic and cathartic salts providing a source of sodium, potassium and magnesium in a proportion which maintains a normal electrolyte balance of sodium, potassium and magnesium in the body fluids of said mammal.

15. A composition as in claim 14, wherein said composition contains a non-toxic irritant cathartic in an amount effective for emptying the contents of the intestinal tract of said lactating mammal selected from a group consisting of sulfur and barium chloride.

16. A feed composition for removing an accumulation of fluid in mammary tissue of a lactating mammal which contains at least about 0.5 wt.% of an orally administrable composition effective for drawing said fluid from mammary tissue into the intestinal and urinary tracts of said mammal comprising:
  (1) at least one non-toxic diuretic salt in an amount effective for drawing excess fluid from mammary tissue of a lactating mammal into the urinary tract selecting from a group consisting of potassium sulfate, potassium chloride, potassium tartrate, potassium citrate, potassium acetate, potassium nitrate, sodium sulphate, sodium acid phosphate and tribasic sodium phosphate;
  (2) at least one non-toxic saline cathartic salt in an amount effective for drawing fluid from mammary tissue into the intestinal tract of said lactating mammal which is selected from the group consisting of potassium sulfate, potassium chloride, sodium sulfate, sodium citrate, magnesium sulfate, magnesium phosphate, magnesium oxide, magnesium hydroxide, magnesium tartrate, and magnesium carbonate; and
said diuretic and cathartic salts providing a source of sodium, potassium and magnesium in a proportion which maintains a normal electrolyte balance in the body fluids of said mammal.

17. A feed composition as in claim 16, wherein said orally administered composition contains a non-toxic irritant cathartic in an amount effective for emptying the contents of the intestinal tract of said lactating mammal selected from a group consisting of sulfur and barium chloride.

18. A method of removing an accumulation of fluid in mammary tissue of a lactating mammal comprising; orally administrating a non-toxic composition in an amount effective for drawing fluid from said mammary tissue into the intestinal and urinary tracts of said mammal which contains:
  (1) at least one non-toxic diuretic salt in an amount effective for drawing excess fluid from mammary tissue of a lactating mammal into the urinary tract selecting from a group consisting of potassium sulfate, potassium chloride, potassium tartrate, potassium citrate, potassium acetate, potassium nitrate, sodium sulphate, sodium acid phosphate and tribasic sodium phosphate;
  (2) at least one non-toxic saline cathartic salt in an amount effective for withdrawing fluid from mammary tissue into the intestinal tract of said lactating mammal selected from the group consisting potassium sulfate, potassium chloride, sodium sulfate, sodium chloride, sodium phosphate, sodium tartrate, sodium citrate, magnesium sulfate, magnesium phosphate, magnesium oxide, magnesium hydroxide, magnesium tartrate, and magnesium carbonate; and
said diuretic and cathartic salts providing a source of sodium, potassium and magnesium in a proportion which maintains a normal electrolyte balance in the body fluids of said mammal.

19. A method as in claim 18, wherein said composition which is orally administered contains a non-toxic irritant cathartic in an amount effective for emptying the contents of the intestinal tract of said lactating mammal selected from a group consisting of sulfur and barium chloride.

* * * * *